United States Patent

Tang et al.

Patent Number: 5,262,542

Date of Patent: Nov. 16, 1993

[54] PROCESS FOR PREPARATION OF 1H-PYRAZOLO [1,5-B][1,2,4]TRIAZOLE COMPOUNDS BY CYCLIZATION OF N-(4-SUBSTITUTED-PYRAZOLYL)AMIDOXIME

[75] Inventors: Ping-Wah Tang; Terrence C. Mungal, both of Rochester, N.Y.

[73] Assignee: Eastman Kodak Company, Rochester, N.Y.

[21] Appl. No.: 841,463

[22] Filed: Feb. 26, 1992

[51] Int. Cl.$^5$ .................... C07P 487/04; G03C 7/38; G03C 7/407
[52] U.S. Cl. ........................... 548/262.4; 548/329.1
[58] Field of Search ............... 548/262.4, 329.1

[56] References Cited

U.S. PATENT DOCUMENTS

| | | | |
|---|---|---|---|
| 4,540,654 | 9/1985 | Sato et al. | 548/262.4 X |
| 4,621,046 | 11/1986 | Sato et al. | 548/262.4 X |
| 4,705,863 | 11/1987 | Sato et al. | 548/262.4 X |
| 4,921,968 | 5/1990 | Yokoyama et al. | 548/262.4 |

FOREIGN PATENT DOCUMENTS

| | | | |
|---|---|---|---|
| 287265 | 10/1988 | European Pat. Off. | 548/262.4 |
| 60-172982 | 9/1985 | Japan | 548/262.4 |
| 60-197688 | 9/1985 | Japan | 548/262.4 |
| 60-215687 | 10/1985 | Japan | 548/262.4 |
| 63-218665 | 9/1988 | Japan | 548/262.4 |
| 1-025765 | 1/1989 | Japan | 548/262.4 |
| 2-161430 | 6/1990 | Japan | 548/262.4 |

*Primary Examiner*—Floyd D. Higel
*Attorney, Agent, or Firm*—Wegner, Cantor, Mueller & Player

[57] ABSTRACT

A process of preparing 1H-pyrazolo [1,5-b][1,2,4] triazole compounds represented by formula (I):

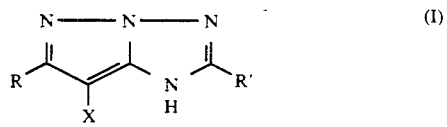

wherein R and R' independently represent H or a substituent, and X represents a coupling-off substituent, comprises subjecting an amidoxime of formula (II)

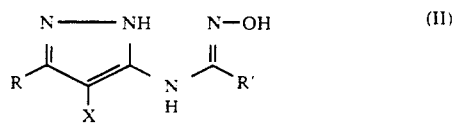

to a cyclization reaction to obtain the compound of formula (I).

9 Claims, No Drawings

PROCESS FOR PREPARATION OF 1H-PYRAZOLO [1,5-B][1,2,4]TRIAZOLE COMPOUNDS BY CYCLIZATION OF N-(4-SUBSTITUTED-PYRAZOLYL)AMIDOXIME

The present invention relates to a process of preparing 1H-pyrazolo [1,5-b][1,2,4] triazole compounds represented by formula (I):

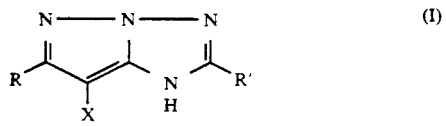

Formula (I) includes pyrazolotriazole compounds which are useful as dye-forming 1H-pyrazolo [1,5-b][1,2,4] triazole couplers employed in photographic silver halide materials, wherein R and R' are independently hydrogen or coupler substituents known in the photographic art which do not adversely affect the desired properties of the coupler, and X is a coupling-off group, other than hydrogen, known in the photographic art. Such couplers are described in European Patent 177,765 and U.S. Pat. No. 4,540,654, for example. Additionally, formula (I) includes compounds wherein R or R' is a reactive group which can be converted to the coupler substituent, thereby providing a dye-forming 1H-pyrazolo [1,5-b][1,2,4] triazole coupler.

In a first aspect, the process comprises subjecting an amidoxime of formula (II)

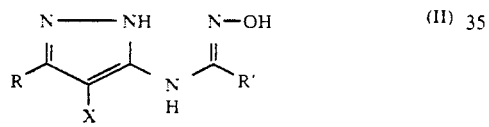

to a cyclization reaction to obtain the compound of formula (I), wherein R, R' and X in formula (II) are as defined for formula (I).

In a second aspect, the process includes the production of amidoximes of formula (II) by reacting a compound of formula (III)

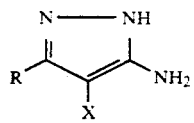

with NH$_2$OH or a salt thereof and a compound of formula (IV)

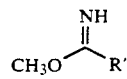

or a salt thereof to obtain an amidoxime of formula (II). R, R' and X are as defined above.

Japanese kokai 60-215,687 discloses a process for preparing 1H-pyrazolo [1,5-b][1,2,4] triazole compounds which contain hydrogen in the 4-position of the pyrazole ring from an amidine. However, this process employs a highly toxic oxidizing agent, Pb(OAc)$_4$, and requires chromatography to isolate the desired product. Additionally, the process yields the product in unsatisfactorily low yields.

U.S. Pat. No. 4,705,863 describes ring closure of an amidoxime compound having a pyrazolyl group to produce 1H-pyrazolo [1,5-b][1,2,4] triazole compounds which contain hydrogen in the 4-position of the pyrazole ring.

It is an object of the present invention to provide improved methods for the production of 1H-pyrazolo [1,5-b][1,2,4] triazole compounds. The process of the present invention overcomes the drawbacks of prior art processes, as the reaction mechanism is relatively simple, avoids the use of toxic materials, and provides products in higher yields.

DESCRIPTION OF THE PREFERRED EMBODIMENTS

In a preferred embodiment, the process is represented by the following scheme:

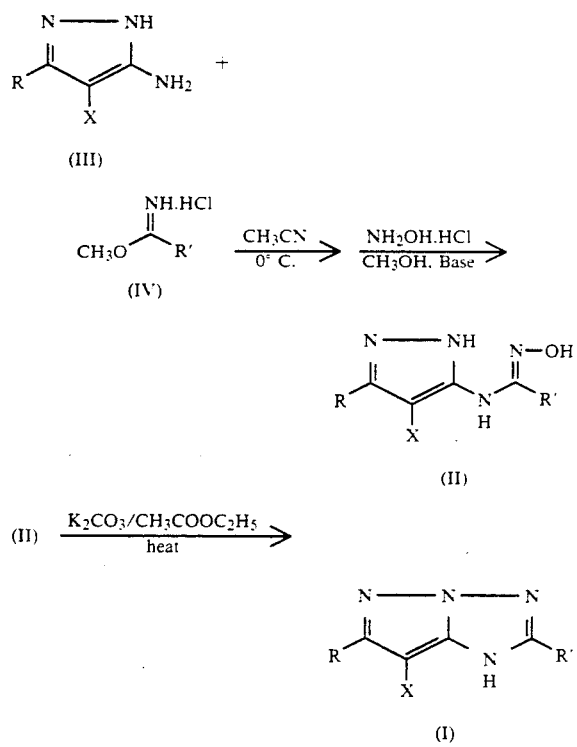

The preparation of the amidoxime of formula (II) from the aminopyrazole of formula (III) and the imidate of formula (IV) is preferably conducted in a solvent such as acetonitrile or a protic solvent (e.g., methanol, ethanol, propanol or isopropanol). While these solvents are preferred, other solvents which are inert with respect to the reactants and products and satisfactorily dissolve the subject materials can be employed. Examples of other suitable solvents are ether, tetrahydrofuran, dioxane, etc. Mild reaction temperatures, such as −5° C. to 45° C., are employed with ambient pressure and a reaction time of 0.5 hour to 8 hours. A base is necessary for the step of formation of amidoxime of formula (II). Preferred bases are alkali metal salts of lower alcohols, such as sodium methoxide, lithium methoxide, sodium ethoxide, etc.

In the cyclization step, the amidoxime of formula (II) is cyclized to yield the desired 1H-pyrazolo [1,5- b][1,2,4] triazole compound. The reaction is carried out in the presence of a base. Preferred bases are alkali metal salts of weak acids in which the metal is Li, Na or K. Thus, preferred salts are $K_2CO_3$, $KHCO_3$, $Na_2CO_3$, $Li_2CO_3$, etc. although other materials may be employed in the method according to the present invention.

Illustrative 1H-pyrazole [1,5-b][1,2,4] triazole compounds of formula (I) which can be produced according to the present invention are as follows. Each of the following compounds are useful as a dye-forming coupler, and each contains a ballast group for R' in formula (I).

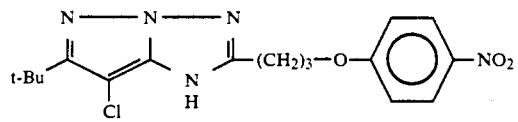
M1

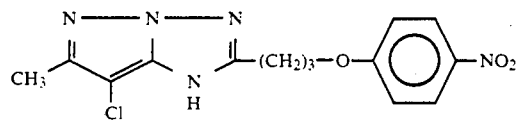
M2

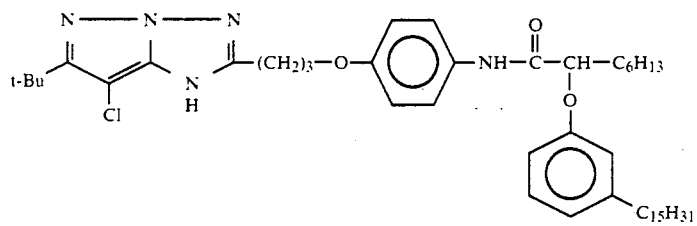
M3

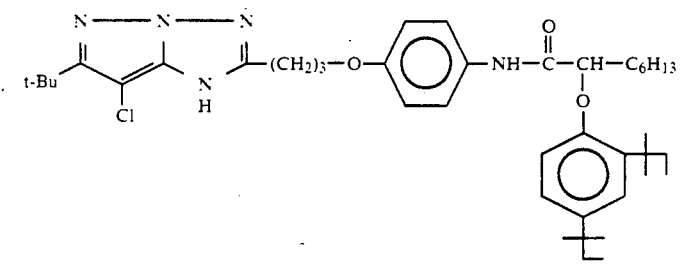
M4

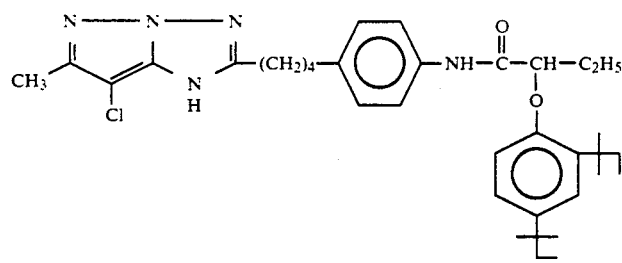
M5

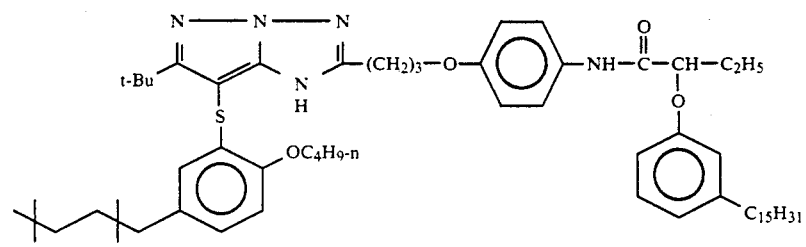
M6

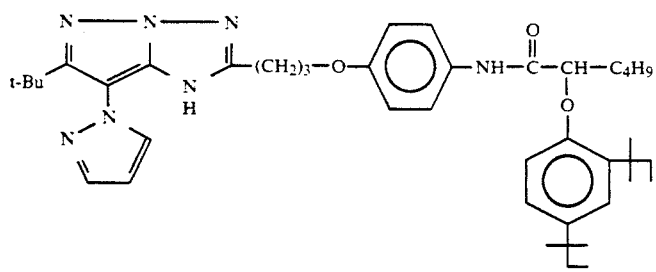

In the above formulae, X is a coupling-off group known in the art. Coupling-off groups are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclicimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U.K. patents and published application numbers 1,466,728; 1,531,927; 1,533,039; 2,006,755A and 2,107,704A; the disclosures of which are incorporated herein by reference.

Examples of specific coupling-off groups are

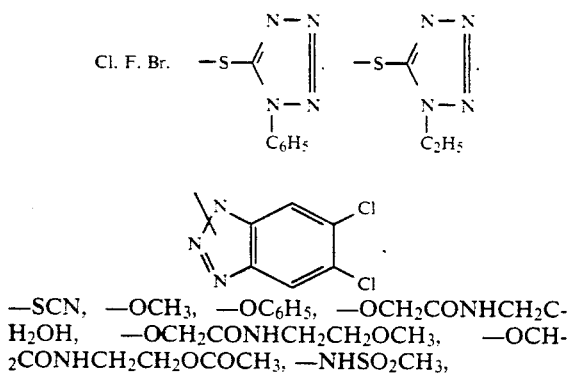

—SCN, —OCH$_3$, —OC$_6$H$_5$, —OCH$_2$CONHCH$_2$CH$_2$OH, —OCH$_2$CONHCH$_2$CH$_2$OCH$_3$, —OCH$_2$CONHCH$_2$CH$_2$OCOCH$_3$, —NHSO$_2$CH$_3$,

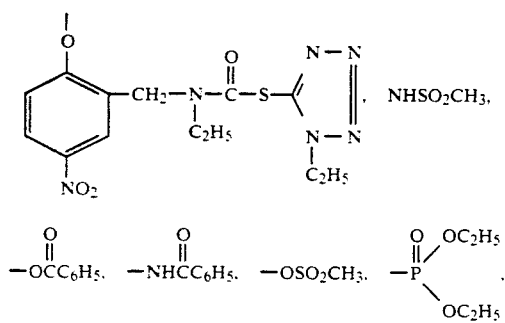

—OCC$_6$H$_5$, —NHCC$_6$H$_5$, —OSO$_2$CH$_3$, $-P\begin{smallmatrix}O\\\diagup\\\diagdown\end{smallmatrix}\begin{smallmatrix}OC_2H_5\\\\OC_2H_5\end{smallmatrix}$

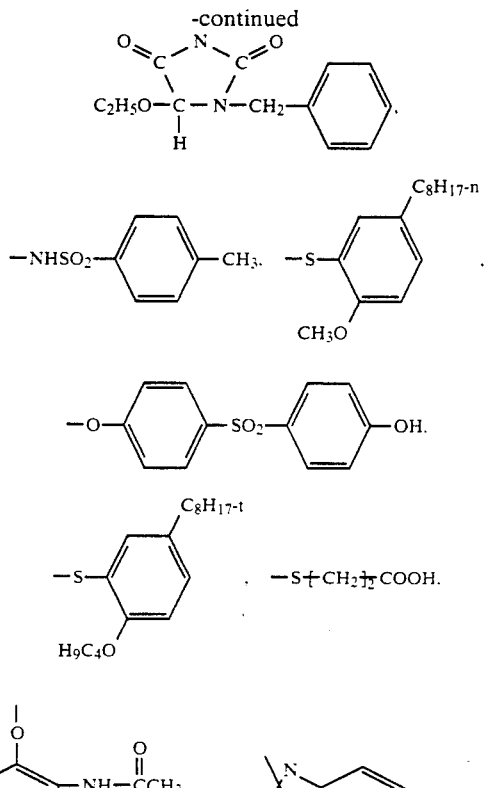

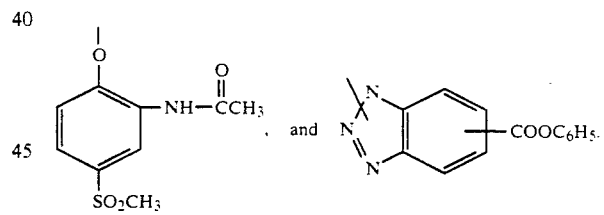

X as chlorine, bromine or —S—Ar, wherein Ar is an unsubstituted or substituted phenylene group, are especially advantageous for the method according to the present invention, with X as chlorine being particularly preferred.

R and R' independently represent hydrogen substituent known in the art which typically promotes solubility, diffusion resistance or dye hue or dye stability of the dye formed upon reaction of the coupler with the oxidized color developing agent.

Examples of such substituent groups include: an alkyl group which may be straight or branched, and which may be substituted, such as methyl, ethyl, n-propyl, n-butyl, t-butyl, trifluoromethyl, tridecyl or 3-(2,4-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N,N-dipropylsulfamoylamino or N-methyl-N-decylsulfamoylamino.

Additional examples of substituent groups include: a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycaronylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy) acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group carbon atoms which may be substituted; a carboxyl group which may be substituted; a sulfo group which may be substituted; hydroxyl; an amino group which may be substituted; or a carbonamido group which may be substituted.

Substituents for the above substituted R or R' groups include those that do not adversely affect the desired properties of the pyrazolotriazole coupler. Representative substituents for the substituted R or R' groups include: halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

Generally, the above groups and substituents thereof which contain an alkyl group may include an alkyl group having 1 to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

Preferably, R or R' represents hydrogen, an alkyl group, an aryl group, a carbonamido group, a sulfonamido group, a sulfone group, a thio group, a sulfoxide group, a ureido group or a multicyclic group.

Additionally, several of the above described R or R' groups constitute a ballast group, which is known in the photographic art as a radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups on the pyrazolotriazole nucleus. For example, one or more coupler moieties can be attached to the same ballast group. Representative ballast groups include substituted or unsubstituted alkyl or alkoxy or aryloxy or aryl groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido, and sulfamoyl substituents containing 1 to 30 carbon atoms and 6 to 30 carbon atoms, respectively, can be further substituted with such substituents.

Additionally, R or R' in formula (I) may constitute a reactive group which can be converted to a coupler substituent as defined above, thereby providing a dye-forming 1H-pyrazolo [1,5-b][1,2,4] triazole coupler. Thus, formula (I) includes compounds produced according to the method of the present invention which can then be further modified through the R or R' substituent to provide a desired dye-forming 1H-pyrazolo [1,5-b][1,2,4] triazole coupler by methods known in the art. For example, when R or R' is amino (—NH$_2$), the amino can be reacted with a group such as R"—CO—Cl, wherein R" is an alkyl, aryl, heterocyclic, alkoxy, aryloxy, alkylamino or arylamino group, to form a substituent of R"—CO—NH— on the pyrazolotriazole ring. An example of such a method is illustrated in U.S. Pat. No. 4,540,654, the disclosure of which is incorporated by reference.]

The following examples illustrate the production of 1H-pyrazolo [1,5-b][1,2,4] triazole compounds according to the process of the present invention, although it is understood that other compounds of formula (I) known in the art can be analogously prepared.

Reaction Scheme

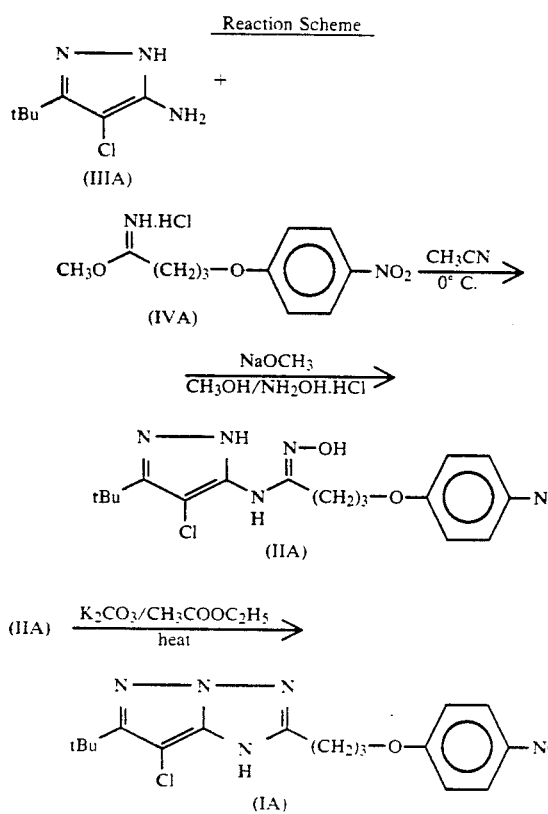

Preparation of Amidoxime (IIA)

A suspension of 145 g (0.835 mol, 1.0 equiv) of 5-amino-3-tert-butyl-4-chloropyrazole (IIIA) in 1000 mL of acetonitrile was cooled to 0° C., followed by the portionwise addition of 240.75 g (0.876 mol, 1.05 equiv) of imidate (IVA). The reaction mixture was stirred at 0° C. for 3 hours. The mixture was concentrated in vacuo to yield a solid. To the solid, 1000 ml of methanol was added, followed by the addition of 63.79 g (0.918 mol, 1.10 equiv) of hydroxylamine hydrochloride. The stirred suspension was cooled to 0° C. followed by the portionwise addition of 198.4 g (0.918 mol, 1.10 equiv) of sodium methoxide (25% w/w in methanol). The reaction was allowed to warm to room temperature and stirred overnight. The mixture was poured into 6.5 liters of an ice-water mixture. The mixture was stirred for 2 hours and the resulting solid was collected under suction, washed and dried in vacuo. The yield of the desired product (IIA) was 285.40 g (86%). All the analytical data were in agreement with the structure.

Preparation of Coupler (IA)

A suspension of 7.91 g (0.02 mol, 1.0 equiv) of amidoxime (IIA) and 11.05 g (0.04 mol, 2.0 equiv) of potassium carbonate in 100 mL of ethyl acetate was heated at reflux for 16 hours under an atmosphere of nitrogen. At that time, no starting material remained as evidenced by thin layer chromatography (TLC) analysis of the reaction mixture. The mixture was allowed to cool to room temperature. It was poured into a mixture of ice water, acidified to a pH value equal to 1-2. The organic product was extracted with ethyl acetate. The combined extracts were washed with three 100-mL portions of a solution of sodium carbonate (10-15%), one 100-mL portion of a diluted solution of hydrochloric acid (5%) and finally two 100-mL portions of water. The organic layer was dried over anhydrous magnesium sulfate and filtered. The filtrate was concentrated in vacuo to yield an oil which solidified upon standing. The yield of the desired product (IA) was 3.2 g (42%). Mass analysis $M^+ = 378$. Proton NMR was consistent with an authentic sample.

The invention has been described in detail with particular reference to preferred embodiments thereof, but it will be understood that variations and modifications can be effected within the spirit and scope of the invention.

What is claimed is:

1. A process of preparing a 1H-pyrazolo [1,5-b][1,2,4] compound of formula (I)

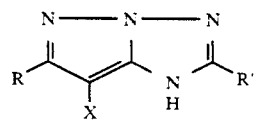

wherein R and R' independently represent H or a substituent selected from the group consisting of a coupler substituent, a ballast group, and a reactive group which can be converted to a coupler substituent, and X represents a coupling-off substituent and excludes hydrogen, said process comprising subjecting an amidoxime of formula (II)

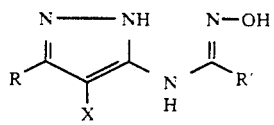

wherein R, R', and X are as previously defined, to a cyclization reaction in the presence of an alkali metal salt of a weak acid to obtain the compound of formula (I).

2. The process of claim 1, wherein X is Cl.
3. The process of claim 2, wherein R is an alkyl group or a multicyclic hydrocarbon group.
4. The process of claim 2, wherein R' is a ballast group.
5. The process of claim 1, wherein the cyclization is conducted in the presence of $K_2CO_3$ and $CH_3COOC_2H_5$ at an elevated temperature.
6. The process of claim 5, wherein X is Cl.
7. The process of claim 1, wherein the cyclization is conducted in the presence of $K_2CO_3$ and $CH_3COOC_2H_5$ at an elevated temperature.
8. The process of claim 7, wherein X is Cl.
9. The process of claim 1 wherein the metal of said alkali metal salt of a weak acid is lithium, sodium or potassium.

* * * * *